(12) United States Patent
Rosen et al.

(10) Patent No.: US 7,238,682 B1
(45) Date of Patent: Jul. 3, 2007

(54) METHODS AND COMPOSITIONS FOR DEGRADATION AND/OR INHIBITION OF HER-FAMILY TYROSINE KINASES

(75) Inventors: Neal Rosen, Englewood, NJ (US); Scott D. Kuduk, New York, NY (US); Samuel J. Danishefsky, Englewood, NJ (US); Furzhong F. Zheng, New York, NY (US); Laura Sepp-Lorenzino, New Haven, CT (US); Ouatek Ouerfelli, New York, NY (US)

(73) Assignee: Sloan-Kettering Institute for Cancer Research, New York, NY (US)

(*) Notice: Subject to any disclaimer, the term of this patent is extended or adjusted under 35 U.S.C. 154(b) by 0 days.

(21) Appl. No.: 09/937,192

(22) PCT Filed: Apr. 7, 2000

(86) PCT No.: PCT/US00/09512

§ 371 (c)(1),
(2), (4) Date: Sep. 21, 2001

(87) PCT Pub. No.: WO00/61578

PCT Pub. Date: Oct. 19, 2001

Related U.S. Application Data (60) Provisional application No. 60/128,593, filed on Apr. 9, 1999.

(51) Int. Cl.
*C07D 403/02* (2006.01)
*A61K 31/395* (2006.01)
*A61P 35/00* (2006.01)

(52) U.S. Cl. ..................... 514/183; 540/461
(58) Field of Classification Search ............... 540/461; 514/183
See application file for complete search history.

(56) References Cited

U.S. PATENT DOCUMENTS

| 4,261,989 A | 4/1981 | Sasaki et al. ............... 424/244 |
| 5,650,430 A | 7/1997 | Sugimura et al. ............ 514/450 |
| 5,932,566 A | 8/1999 | Schnur et al. ............... 514/183 |
| 5,968,921 A | 10/1999 | Gold ......................... 514/183 |
| 6,239,168 B1 | 5/2001 | Ino et al. .................... 514/450 |

OTHER PUBLICATIONS

Munster et al., "Inhibition of Heat Shock Protein 90 Function by Ansamycins Causes the Morphological and Functional Differentiation of Breast Cancer Cells", *Cancer Research*. Apr. 1, 2001, vol. 61, pp. 2945-2952.

Schulte et al., "The benzoquinone ansamycin 17-allylamino-17-demethoxygeldanamycin binds to HSP90 and shares important biologic activities with geldanamycin", *Cancer Chemotherapy and Pharmacology*, 1998, vol. 42, pp. 273-279.

Bohen, S.P., "Genetic and Biochemical Analysis of p23 and Ansamycin Antibiotics in the Function of HSP90-Dependent Signaling Proteins", *Molecular and Cellular Biology*, Jun. 1998, vol. 18, No. 6, pp. 3330-3339.

Pratt, W.B., "The hsp90-based Chaperone System: Involvement in Signal Transduction from a Variety of Hormone and Growth Factor Receptors", Proceedings of the Society for Experimental Biology and Medicine, Apr. 1998, vol. 217, No. 4, pp. 420-434.

Scheibel, et al., "Two chaperone sites in Hsp90 differing in substrate specificity and ATP dependence", Proceedings of the National Academy of Sciences of the USA, Feb. 17, 1998, vol. 95, No. 4, pp. 1495-1499.

Chen, et al., "The Ah Receptor is a Sensitive Target of Geldanamycin-Induced Protein Turnover", *Archives of Biochemistry and Biophysics*, Dec. 1, 1997, vol. 348, No. 1, pp. 190-198.

Landel, et al., "Estrogen Receptor Accessory Proteins Augment Receptor-DNA Interaction and DNA Bending", *The Journal of Steroid Biochemistry & Molecular Biology*, vol. 63, No. 1-3, pp. 59-73.

Bamberger, et al., "Inhibition of Mineralocorticoid and Glucocorticoid receptor function by the heat shock protein 90-binding agent geldanamycin", *Molecular and Cellular Endocrinology*, Aug. 8, 1997, vol. 131, No. 2, pp. 233-240.

Segnitz, et al., "The Function of Steroid Hormone Receptors s Inhibited by the hsp90-specific Compound Geldanamycin", *The Journal of Biological Chemistry*, Jul. 25, 1997, vol. 272, No. 30, pp. 18694-18701.

Hurst, S. et al., "HSP90 inhibitors block the mitotic checkpoint and are synergistically toxic with spindle poisons", *Clinical Cancer Res.*, Nov. 1999, vol. 8, p. 3788s, #293.

Kherfellah, d. et al, "Effect of the combination of topoisomerase I and topoisomerase II inhibitors on rat glioblastoma cells and drug-resistant variants", *Pharmacol. Experimental Therapeutics*, Mar. 1999, vol. 40, p. 109, #724.

Stebbins, c. E. et al, "Crystal structure of the Hsp90-Geldanamycin complex: targeting of a protein chaperone by an antitumor agent", *Cell*, Apr. 1997, vol. 89, pp. 239-240 and 246-248.

Rosenhagen, M. C. et al, "Synergistic inhibition of the Glucocorticoid receptor by radicicol and benzoquinone ansamycins", *Biol. Chem.*, Mar. 2001, vol. 382, pp. 499-504.

(Continued)

*Primary Examiner*—Bruck Kifle
(74) *Attorney, Agent, or Firm*—Marina Larson & Associates, LLC (57) ABSTRACT

Bifunctional molecules comprising two hsp-binding moieties which bind to hsp90 in the pocket to which ansamycin antibiotics bind connected via a linker are effective for inducing the degradation and/or inhibition of HER-family tyrosine kinases. For example, a compound of two geldanamycin moieties joined by a four-carbon linker provides selective degradation of HER-family tyrosine kinases, without substantially affecting other kinases. These compounds can be used for treatment of HER-positive cancers with reduced toxicity, since these compounds potently kill cancer cells but affect fewer proteins than geldanamycin.

29 Claims, 3 Drawing Sheets

OTHER PUBLICATIONS

Chavany et al. "p185$^{crbB2}$ Binds to GRP94 in Vivo", Journal of Biological Chemistry, vol. 271, No. 9 Mar. 1, 1996, pp. 4974-4977.

Neckers, "Effects of Geldanamycin and Other Naturally Occurring Small Molecule Antagonists of Heat Shock Protein 90 on HER2 Protein Expression", Breast Disease 11 (2000) 49-59. pp. 49-59.

Schnur, et al. "erbB-2 Oncogene Inhibition by Geldanamycin Derivatives: Synthesis, Mechanism of Action, and Structure—Activity Relationships", J. Med. Chem. 1995, 38, 3813-3820.

Glonek, $^{31}$P NMR of Mg-ATP in Dilute Solutions: Complexation and Exchange, Int. J. Biochem, 1992, pp. 1533-1559, vol. 24, No. 10.

Haystead et. al., γ-Phosphate-linked ATP-Sepharose for the affinity purification of pretein kinases, Eur. J. Biochem., 1993, pp. 459-467, vol. 214.

Prodromou et. al., Identification and Structural Characterization of the ATP/ADP-Binding Site in the Hsp90 Molecular Chaperone, Cell, Jul. 11, 1997, pp. 65-75, vol. 90.

METHODS AND COMPOSITIONS FOR DEGRADATION AND/OR INHIBITION OF HER-FAMILY TYROSINE KINASES

This application is a 371 of International Application No. PCT/US00/09512, filed Apr. 7, 2000, which claims the benefit of U.S. Provisional Application No. 60/128,593 filed Apr. 9, 1999.

TECHNICAL FIELD

This application relates to bifunctional molecules having two moieties which interact with the chaperone protein hsp90, including in particular homo- and heterodimers or ansamycin antibiotics. These bifunctional molecules act to promote degradation and/or inhibition of HER-family tyrosine kinases and are effective for treatment of cancers which overexpress Her-kinases.

BACKGROUND ART

Targeted delivery of therapeutic agents as a means for treating cancer has been proposed by many authors. Conceptually, the idea is to deliver a toxic substance selectively to the cancer cells, thus reducing the general toxicity to the patient. This is theoretically possible, since many cancer cell types have been found to have increased levels of hormone receptors and similar receptors. For example, breast cancer cells may have elevated levels of HER2 receptors or estrogen receptors which result in hormone-stimulated growth of cancer cells, while androgen receptors are required for growth of many prostate cancers and mutation of the androgen receptors frequently occurs in advanced prostate cancer.

Hormone receptors have been used in studies on the feasibility of using direct targeted chemotherapy agents to certain classes of cells. Thus, for example, Lam et al., *Cancer Treatment Reports* 71: 901–906 (1987) have reported on estrogen-nitrosourea conjugates as potential cytotoxic agents against human breast cancer, while Brix et al., *J. Cancer Res.* 116: 583–539 (1990) have reported on studies of the use of androgen-linked alkylating agents as antineoplastic agents. See also, Eisenbrand et al., *Acta Oncologica* 28: 203–211 (1989). Myers and Villemez, *Biochem. Biophys. Res. Commun.* 163: 161–164 (1989) have disclosed the possibility of utilizing luteinizing hormone coupled to a truncated diphtheria toxin.

Geldanamycin (GM) and herbimycin A (HA) are natural benzoquinoid ansamycin antibiotics. Uehara, et al., *Mol. Cell. Biol.* 6, 2198–2206 (1986). This class of drugs binds to a specific pocket in the chaperone protein hsp90. Stebbins, C. E. et al., *Cell* 89, 239–250 (1997); Prodromou, et al., *Nat Struct Biol* 4, 477–482 (1997). Occupancy of this pocket by the drug leads to the degradation in the proteasome of a subset of proteins that require hsp90 for conformational maturation. Schneider, et al., *Proc. Natl. Acad. Sci.* (USA) 93, 14536–14541 (1996); Csermely, et al., *Pharmacol Ther* 79, 129–168 (1998); Scheibel, et al., *Biochem Pharmacol* 56, 675–682 (1998). These include the HER- and insulin-receptor family of transmembrane tyrosine protein kinases, Raf serine kinase and steroid receptors. Addition of GM to tumor cells leads to an Rb-dependent G1 growth arrest and apoptosis. HER-kinases are among the most sensitive targets of GM and tumor cell lines in which HER2 is overexpressed are inhibited by especially low concentrations of the drug. Miller, et al., *Cancer Res* 54, 2724–2730 (1994); Schnur, et al., *J. Med. Chem.* 38, 3806–3812 (1995); Hartmann, et al., *Int J Cancer* 70, 221–229 (1997). These findings imply that GM and related drugs may be useful in the treatment of a variety of tumors. An analog of GM, 17-allyaminoGM, will soon be studied in phase I clinical trials. However, the number of important signaling molecules that are affected by ansamycins suggests that they may have untoward toxicity. In addition, benzoquinoid antibiotics can induce the selective degradation in vivo of receptors, including estrogen, androgen and progesterone receptors. International Patent Publication No. WO98/51702 discloses the ability of compositions comprising an ansamycin antibiotic or other hsp90 binding moiety and a targeting moiety which specifically binds to a target protein to stimulate the selective degradation of such target proteins, and the use of such compositions as chemotherapy agents.

HER-family transmembrane receptor tyrosine kinases play an important role in transducing extracellular growth signals and when activated can be oncogenic. Tzahar, et al., *Biochim Biophys Acta* 1377, M25–37 (1998); Ross, et al., *Stem Cells* 16, 413–428 (1998). Over-expression of HER1 and HER2 occurs in a variety of human malignancies. Amplification of the HER2 gene is a common event in human breast and other carcinomas and, in breast cancer, is associated with a poor prognosis. HER1 and HER2 are attractive targets for therapeutic development. Antibodies against each of these receptors have been shown to have antitumor effects in animal models. Fan, et al., *Curr Opin Oncol* 10, 67–73 (1998). Recently, an anti-HER2 antibody was shown to be effective in the treatment of breast cancers in which the HER2 protein is overexpressed. Ross et al., supra; Pegram, et al., *J Clin Oncol* 16, 2659–2671 (1998). However, therapeutic effects were seen in only a minority of patients and were usually short-lived. It is not known whether this is due to inefficient inhibition of the target by the antibody, but clearly other more effective methods for HER2 inhibition are needed.

Thus, notwithstanding efforts to date, there remains a substantial need for compositions which can be utilized to selectively target and degrade HER-family tyrosine kinases which can be used as chemotherapy agents in the treatment of HER-expressing cancers, including Her2 positive breast cancer. It is an object of the present invention to provide such compositions.

It is a further object of the present invention to provide a method for the treatment of Her-positive cancers.

DISCLOSURE OF THE INVENTION

We have now found that bifunctional molecules comprising two linked hsp-binding moieties which bind to hsp90 in the pocket to which ansamycin antibiotics bind are effective for inducing the degradation and/or inhibition of HER-family tyrosine kinases. For example, a composition having the structure Dimers: n = 1-9 provides selective degradation and/or inhibition of HER-family tyrosine kinases, without substantially affecting other kinases. Thus, the compositions of the invention can be used for treatment of HER-positive cancers with reduced toxicity, since these compounds potentially kill cancer cells but affect fewer proteins than geldanamycin.

MODES FOR CARRYING OUT THE INVENTION

The compounds of the invention are a new class of bifunctional molecules comprising two hsp-binding moieties that bind to hsp90 in the pocket to which ansamycin antibiotics bind, connected to each other by a linker. Preferred compounds are those in which at least one, and more preferably both of the hsp-binding moieties are ansamysin antibiotics such as geldanamycin or herbimycin.

The two hsp-binding moieties are joined by a linker. As discussed in more detail below, this linker may be of varying lengths. Altering the length of the linker results in different activity levels and specificity profiles. In general, the linker will be 1 to 9 carbon atoms in length, and may be a linear carbon chain or a substituted carbon chain, for example incorporating double or triple bonds, an aryl group or a secondary or tertiary amine. (See FIG. 1)

Figure 1:
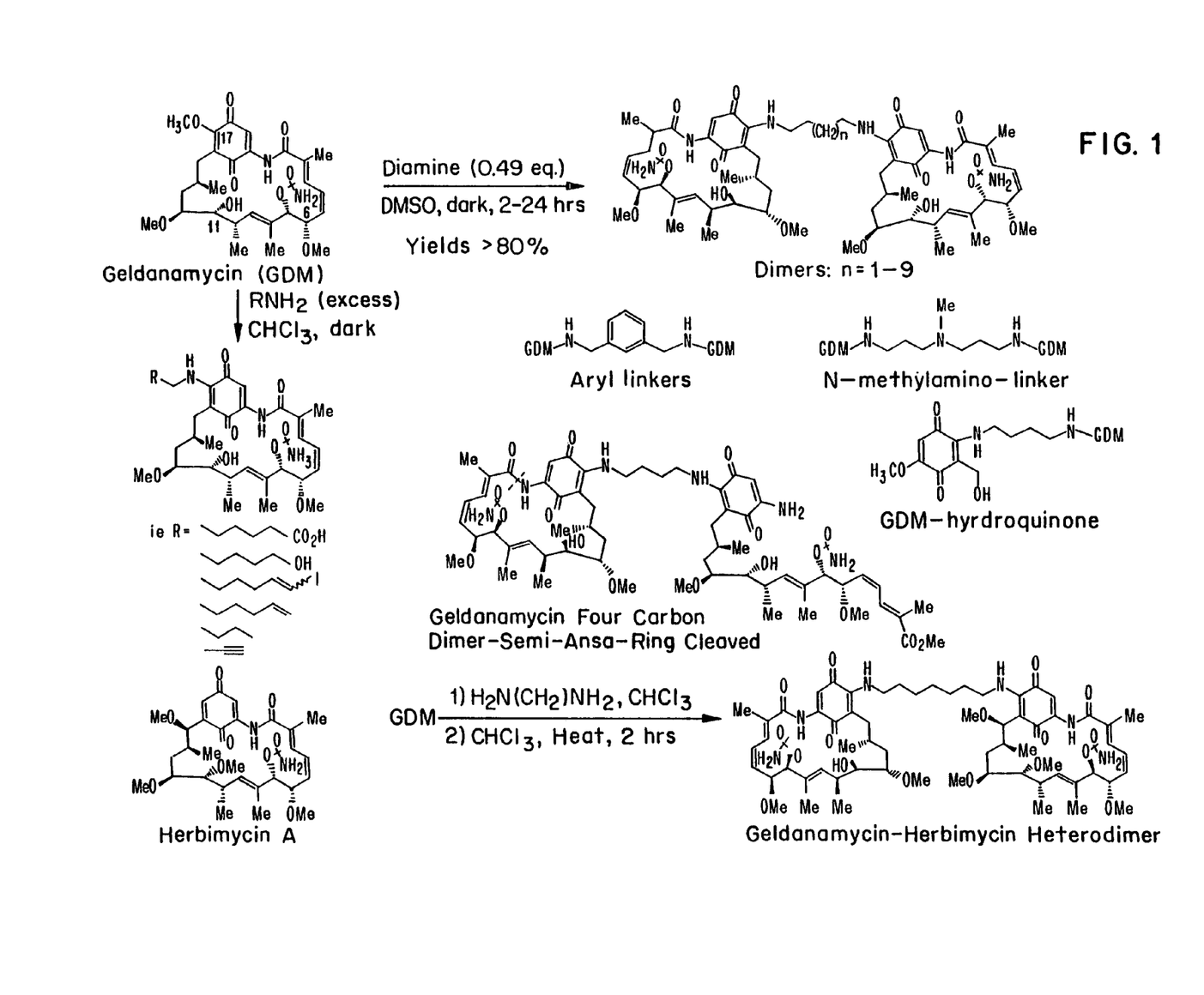
FIG. 1 shows a synthetic scheme for the preparation of compounds in accordance with the invention.

Compounds in accordance with the invention can be synthesized in accordance with the scheme set forth in FIG. 1. In the case of a homodimer, reaction of an ansamycin antibiotic such as geldanamycin with a diamine of appropriate length and structure in DMSO results in the preparation of homodimers in substantial yield. For preparation of a heterodimer, the ansamycin antibiotic such as geldanamycin is first reacted with a primary monoamine, having a second, non-amine functional group. The resulting product is in turn covalently coupled via this functional group to the second type of hsp-binding moiety. An example of such a heterodimer which can be made by this method is a geldanamycin-herbimycin heterodimer.

The compounds of the invention are effective to induce degradation and/or inhibition of HER-family tyrosine kinases, but have a narrower spectrum of action and greater selectively than, for example geldanamycin per se. While not intending to be bound by any particular mechanism of action, the activity and selectivity of the compounds of the invention may arise from the fact that extracellular growth factors that bind to HER-kinases cause them to undergo homodimerization or heterodimerization with other members of the family. This activates the tyrosine kinase activity of the constituents of the dimer, causes their autophosphorylation and initiates transduction of the mitogenic signal. Although a direct interaction of hsp90 and HER-kinases has not been convincingly demonstrated, the fact that sensitivity of HER2 and other kinases to geldanamycin requires the catalytic domain of the kinase suggests that hsp90 is likely to interact with the catalytic domain of HER-kinases. As HER-kinase heterodimers are quite sensitive to GM, we speculated that each element of the heterodimer interacts with hsp90. Accordingly, it is believed that the dimers of the invention interact with both subunits of the HER-kinase heterodimers and thus more effectively and specifically target the active form of the HER-kinase. The mechanism of action appears to be based on degradation of the HER-kinases, but may include or in some cases be derived entirely from an inhibition of activity of the HER-kinases.

Figure 2:
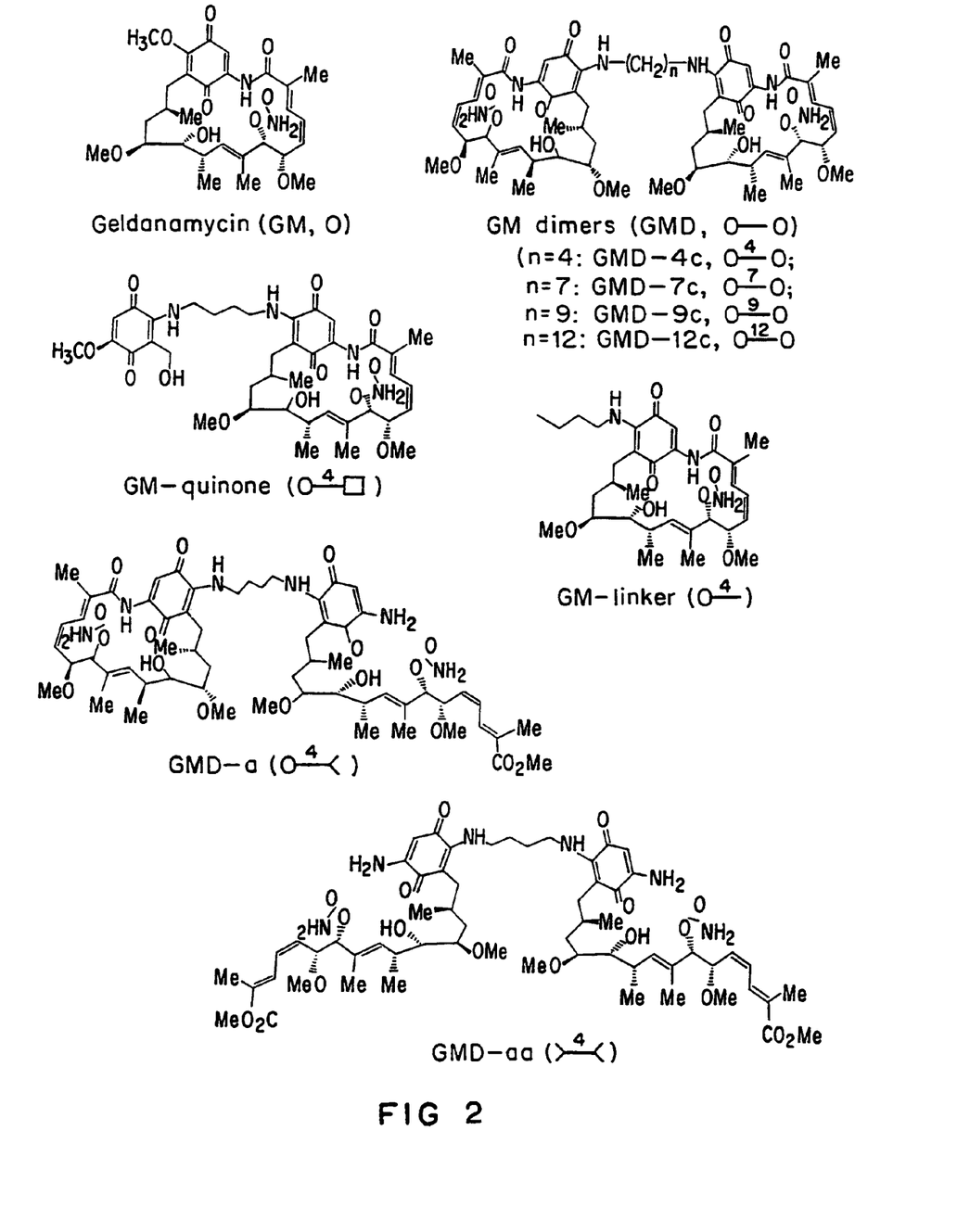
FIG. 2 shows the structures of various compounds synthesized and tested for activity and specificity of action against HER-family tyrosine kinases.

FIG. 2 shows various compounds which have been synthesized and tested for activity and selectivity as promoters of tyrosine kinase degradation. The compounds tested include geldanamycin, geldanamycin homodimers with linkers of varying lengths, species with quinone or ring-opened geldanamycin linked to geldanamycin and geldanamycin coupled to a linker with no substituent at the other end. The linker in each case is bonded to carbon-17 of the geldanamycin moiety or moieties. The crystal structure of GM bound to hsp90 shows that carbon-17 is the only one not buried in the binding pocket. Stebbins, et al., *Cell* 89, 239–250 (1997).

These compounds shown in FIG. 2 were evaluated as described in the examples below, and assessed in terms of efficiency of induction of degradation of the HER2 and Raf protein kinases in MCF-7 cells. The results are summarized in Table 1, where GM moiety is designated as 'O'; carbon linker, as '—'; quinone, as '☐'; the GM moiety with an opened ansaring, as '>' or '<'. As shown, the properties of the geldanamycin dimers vary as a function of linker chain length. GM itself causes the induction of HER2 degradation with an IC50 of 45 nM. Dimers with linkers of four to seven carbons retain activity against HER2 (IC50 60–70 nM).

Dimers with longer linkers lose activity; the twelve carbon-linked compound has an IC50 of 750 nM.

TABLE 1

The effects of geldanamycin analogs on the steady-state levels of HER-2 and Raf-1 and the cell growth of MCF-7.

| Drug[a] | IC50[b] (HER-2) (nM) | IC50[b] (Raf-1) (nM) | IC50[c] (growth inh.) (nM) |
|---|---|---|---|
| O—4—O | 45 | 200 | 25 |
| O—4—O | 60 | 3200 | 100 |
| O—4—< | 500 | 3500 | 650 |
| >—7—< | >5000 | >5000 | >2000 |
| O—9—O | 70 | 500 | 600 |
| O—12—O | 500 | 3800 | 700 |
| O—4—O | 750 | 3500 | 700 |
| O—4— | 80 | 350 | 600 |
| O—4—□ | 55 | 350 | 350 |

Each of the geldanamycin dimers tested showed increased specificity for HER-2 over Raf-1, when compared to GM. The four carbon-linked dimer (GMD-4c) has the greatest selectivity of the compounds tested. GM causes Raf degradation with an IC50 of 200 nM. GMD-4c is much less active, with an IC50 of 3200 nM. Selectivity decreases with increasing chain length; the seven carbon linked-dimer (GMD-7c) retains activity against HER2 (IC50 70 nM) and is only slightly less active than GM against Raf (IC50 500 nM). As linker carbons increase to more than eight, activity against both targets declines in parallel.

The properties of GMD-4c were examined in greater detail by immunoblotting. GM causes the degradation over time of HER-kinases, Raf-1, estrogen receptor and, more slowly, IGF-I receptor. The GMD-4c hybrid molecule reduces HER2 expression with the same kinetics both on Western blot and by immunohistochemical analysis. However, under these conditions GMD-4c does not affect Raf-1 or IGF-I expression. Estrogen receptor levels declined transiently but returned to baseline by 24 hours. A faster migrating HER2-immunoreactive band appeared after 12 hr, predominantly after treatment with GMD-4c. This form accumulates in intracellular vesicles and corresponds to immature HER2. Glycosylation studies revealed that this HER2 form is partially glycosylated and sensitive to endoglycosidase H.

Additional GM derivatives were synthesized to explore the mechanism of selectivity, and the results are summarized in Table 1. ButylaminoGM (GM-linker), a molecule in which the four-carbon linker is attached to one geldanamycin residue, and a four carbon-linked heterodimer of GM and a quinone (GM-quinone), are modestly weaker than GM against both HER2 and Raf-1; they are not selective. GMD-aa, a GMD-4c in which the ansa ring of both of the GM moieties is opened is inactive. GMD-a, a dimer in which the ring of only one of the GM moieties is open has much reduced activity against both targets (IC50 HER2 500 nM, IC50 Raf-1 3500 nM). These data suggest that the selectivity of GMD-4c depends on both GM moieties.

This apparent selectivity could be a property of a weaker or more rapidly metabolized drug which might appear to have selective activity against the most sensitive target (HER2). To address this question, GM and GMD-4c were added to cells at different concentrations and frequencies. Even when GMD-4c was added at high concentrations four times in twelve hours, it retained selectivity. Thus, the rate of metabolism does not appear to be the reason for the observed selectivity.

GMD-4c was also a potent inhibitor of the growth of breast cancer cells containing HER-kinases (Table 1) with an IC50 of 100 nM against MCF-7 compared to IC50 25 nM for GM and 650 nM for the one-ring opened dimer GMD-a. SKBR3 in which HER2 is highly overexpressed was also found to be very sensitive to GMD-4c. Most epithelial cancer cell lines express one or more members of the HER-kinase family. In order to assess whether the effects of GMD-4c on cells were specific, we utilized the 32D hematopoietic cell line. None of the members of the HER-kinase family are expressed in this murine IL3-dependent myeloid progenitor cell line. Wang, et al., *Proc Natl Acad Sci* (USA) 95, 6809–6814 (1998). GM is a potent inhibitor of 32D; GMD-4c does not appreciably affect its growth.

Based on these experimental results, we conclude that GMD-4c induces the selective degradation and/or inhibition of HER-family kinases and specifically inhibits the growth of HER-kinase containing tumor cell lines. This work supports the idea that selective ansamycins with a different, more restricted spectrum of targets than the parent molecules can be synthesized. In this case, the mechanism of selectivity is not yet known, but depends on the presence of both GM moieties and is a function of the length of the linker. GMD-4c may selectively interact with HER-kinase heterodimers, but it is also possible that it preferentially interacts with different hsp90 family members than GM.

HER-kinases are overexpressed in many human tumors, including many breast, ovarian, pancreatic and gastric cancers, and are likely to be important in maintaining the growth of some of them. Anti-HER2 antibodies have activity in the treatment of some breast cancers that overexpress the protein, but the responses are usually partial and of modest duration. The reasons the antibody is of limited utility are unknown, but may relate to incomplete inhibition of HER-kinase function. If so, drugs that destroy these kinases will be much more effective. For this reason, 17-allylamino-geldanamycin, a non-selective ansamycin, is about to be studied in phase 1 trial. GMD-4c is a compound that is effective in destroying HER-kinases, but is likely to be much less toxic than GM, since its effects on other key signaling proteins are attenuated. This represents a new strategy for abrogating growth receptor function in human tumors.

Thus, in accordance with the invention, patients, including human patients having tumor cells that overexpress HER-family tyrosine kinase are treated by administering to the patient a therapeutically effective dose or doses of a chemical compound comprising linked first and second hsp-binding moieties which bind to the pocket of hsp90 with which ansamycin antibiotics bind. Preferred compounds are those in which at least one of the hsp-binding moieties is an ansamycin antibiotic such as geldanamycin. GMD-4c is most preferred. The specific dosage amount utilized will reflect a balancing of efficacy and toxicity, and can be determined only through clinical trials which have not been conducted. The establishment to trial protocols and the determination of the appropriate dosages and treatment frequency is a matter within the skill in the art.

EXAMPLE 1

Geldanamycin was kindly provided by Drs. David Newman and Edward Sausville (Drug Synthesis and Chemistry Branch, National Cancer Instituted), dissolved in 100% dimethylsulfoxide (DMSO) and stored at −20° C. prior to use in preparation of the geldanamycin derivatives of FIG. 2. The GM analogs were prepared according to the procedure depicted in FIG. 1, which is modified from the method of Schnur et al., *J. Med. Chem.* 38, 3813–3820 (1995). Briefly, the geldanamycin dimers (GMDs) were prepared by treatment of GM with 0.5 eq. of the appropriate diamine in DMSO. The ansa ring-opened GMDs (GMD-a and GMD-aa) were prepared by methanolysis (NaOMe/MeOH) of the GMD-4c. GM-quinone was synthesized by first treating GM with excess 1,4-diamobutane, then addition of 2-methoxy-1-hydroxymethylquinone.

For the specific synthesis of the GMD-4c, the following procedure was followed. To a mixture of 10 mg (0.0178 mmol) of geldanamycin in 0.2 mL of DMSO was added 0.94 mL of 1,4-diaminobutane (0.5 eq.). After stirring for 4 hrs in the dark at room temperature, the reaction was judged complete by TLC. The mixture was concentrated and purified via flash chromatography on silica gel (5% MeOH/$CH_2Cl_2$) to afford 8.5 mg of dimer product (85%).

For the specific synthesis of a geldanamycin-herbimycin dimer, the following procedure was followed. To a mixture of GDM (6.1 mg, 0.01 mmol) in 1.5 mL of $CHCl_3$ was added 11.6 mg (10 eq.) of 1,6-diaminohexane in a 2 mL vial. The reaction was stirred at room temperature for one hour in the dark. The chloroform was then washed with water (3×2 mL) and concentrated. To this mixture was added 8.6 mg (0.015 mmol) of herbimycin A and 0.5 mL of $CH_2Cl_2$. The mixture was heated to 40° C. for 24 hours in a sealed vial. The mixture was purified directly via flash chromatography on silica gel (5–7% MeOH/$CH_2Cl_2$) to afford 1.2 mg of C-19 and 3.4 mg C-17 linked (herbimycin numbering) heterodimers (45%).

EXAMPLE 2

The human breast cancer cell lines MCF-7 and SKBR-3 were obtained from ATCC (Rockville, Md.), and maintained in DME/F12 (1:1) supplemented with 10% heat-inactivated fetal bovine serum (Gemini Bioproducts), 2 mM glutamine, and 50 units/ml each of penicillin and streptomycin, in a humidified 5% $CO_2$/air atmosphere at 37° C.

Polyclonal antibodies against HER2 (c-18), Raf-1 (c-12), and P13 kinase (p85) (Z-8) were purchased from Santa Cruz Biotechnology, Inc. A monoclonal antibody against estrogen receptor (clone H-151) was obtained from StressGen Biotechnology Corp. A polyclonal antibody against the β-subunit of IGF-I receptor was kindly provided by Dr. L-H, Wang (Mt. Sinai Medical Center, New York).

Immunoprecipitation and immunoblotting was used to evaluate activity and selectivity of geldanamycin derivatives. MCF-7 cells were exposed to 1 μM geldanamycin or derivative for periods of 3 to 24 hours. After exposure, cells were washed twice with ice-cold phosphate-buffered saline (PBS), collected by scraping and transferred into microcentrifuge tubes. For immunoblotting (HER2, Raf-1, ER), cells were lysed with SDS lysis buffer (50 mM Tris-HCl, pH 7.5, 2% SDS, 10% glycerol, and 1 mM DTT), boiled for 10 min, and sonicated briefly; for immunoprecipitation (IGF-IR), cells were lysed with NP40 lysis buffer (50 mM Tris-HCl, pH 7.5, 1% Nonidet P-40, 150 mM NaCl, 1 mM $Na_3VO_4$, 40 mM NaF, 1 mM phenylmethylsulfonyl fluoride (PMSF) and 10 μg/ml each of aprotinin, leupeptin and soybean trypsin inhibitor) for 20 min at 4° C. Cell lysates were cleared by centrifuging at 14,000×g for 15 min at 4° C. in a microcentrifuge; the supernatants were collected as the experimental samples. Protein concentration in each sample was determined using the BCA kit (Pierce) according to the manufacture's instructions. For detecting IGF-IR, samples were immunoprecipitated with anti-IGF-IR antibody. Immunocomplexes were collected on protein A-Sepharose beads (Pharmacia), washed three times with the lysis buffer. Samples were subjected to SDS-PAGE, electrotransferred to nitrocellulose membranes, detected using the ECL kit (Amersham) according to the manufacturer's protocol, and quantitated using the Gel Doc 1000 (Bio-Rad). IC50 for protein degradation is designated as the amount of each drug needed to degrade 50% of the protein (HER2 or Raf-1) compared to the control in MCF-7 cells after 24-hr treatment.

For cell growth experiments, cells were placed in 6-well tissue-culture plates (Corning) at 20,000 cells/well. Two days after plating, cells were treated with different concentrations of drugs or the vehicle DMSO (0.1%). MCF-7 cells were treated for four days; medium with the appropriate drug or vehicle was changed every 2 days; cells were trypsinized, collected and counted on a Coulter counter; IC50 for cell growth is designated as the amount of each drug needed to inhibit MCF-7 growth by 50% compared to the control vehicle.

Numerical results for IC50 for HER-2, Raf-1 and cell growth are summarized in Table 1, with each number representing the average of three different experiments. GM causes the degradation over time of HER-kinases, Raf-1, estrogen receptor and, more slowly, IGF-I receptor. The GMD-4c hybrid molecule reduces HER2 expression with the same kinetics both on Western blot and by immunohistochemical analysis. However, under these conditions GMD-4c does not affect Raf-1 or IGF-I expression. Estrogen receptor levels declined transiently but returned to baseline by 24 hours.

EXAMPLE 3

To evaluate a possible explanation for the observed selectivity of GMD-4c for degradation of HER-kinase, cells were treated with either geldanamycin or GMD-4c at concentrations of 0.25, 0.5 and 1 μM in varying treatment patterns as follows: single treatment at time 0, treatments at 0 and 3 hours, treatments at 0, and 6 hours, treatments at 0 and 12 hours and treatments at 0, 3, 6 and 12 hours. No significant differences were observed in the amount of HER-2 and Raf-1 as a function of the treatment pattern.

EXAMPLE 4

Murine hematopoietic cell line 32D, which lacks HER-kinases, was kindly provided by Dr Yosef Yarden (The Weizmann Institute of Science, Israel), and maintained in RPMI-1640 supplemented with 10% heat-inactivated FBS, 2 nm interleukin 3 (R&D systems), 2 mM glutamine, and 50 units/ml each of penicillin and streptomycin.

Figure 3:
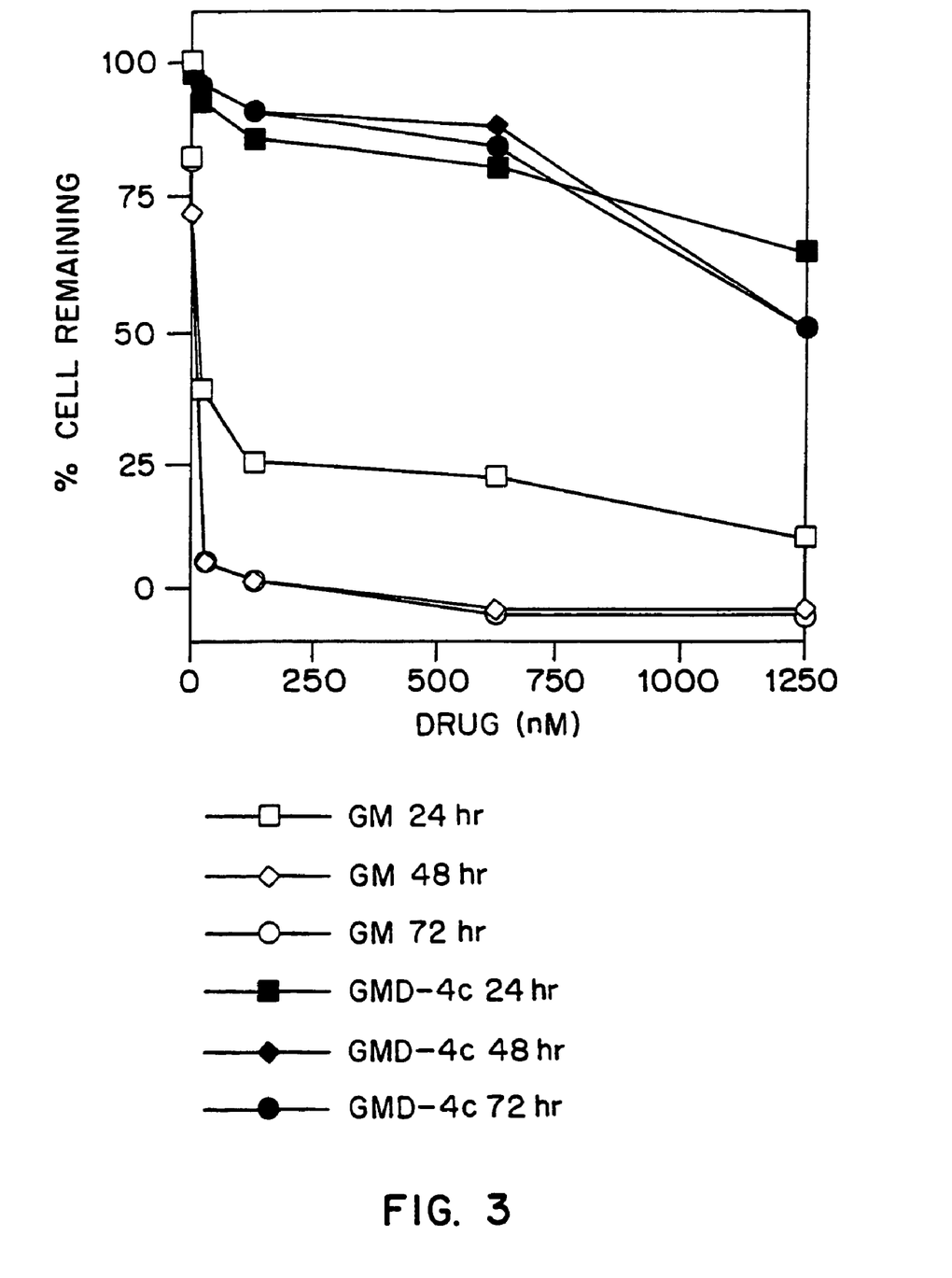
FIG. 3 shows the effect of geldanamycin and GMD-4c on 32D cells was evaluated after treatment with various concentrations.

The effect of geldanamycin and GMD-4c on 32D cells was evaluated after treatment with various concentrations of compound by counting the number of cells every day for three consecutive days using a hematocytometer. The results are summarized in FIG. 3. As shown, geldanamycin was very toxic to these cells, but GMD-4c was much less so, thereby confirming the selectivity of action of GMD-4c against cells expressing HER-family tyrosine kinases.

EXAMPLE 5

MCF-7 cells were grown and treated on fibronectin-coated coverslips placed in multiwell plates. Cells were fixed for 20 min at −20° C. in 100% methanol, rehydrated in PBS for 10 min at room temperature and blocked for 30 min at 37° C. in a blocking solution consisting of 2% bovine serum albumin (BSA), 10% normal goal serum and 0.05% Tween-20 in PBS, HER2 and Raf-1 were immunodetected with antibodies from Santa Cruz (SC284 and SC133, respectively); IGF-IR, an antibody from Calbiochem Oncogene Science (AB1). Slides were incubated with a 11000 dilution of the primary antibody in blocking buffer for 1 hr at room temperature, followed by an incubation with Alexa 546-coupled goat anti-rabbit IgG secondary antibody (A-11010, Molecular Probes) at a 150 dilution in blocking buffer, or fluoresceine isothiocyanate-coupled goat anti-mouse IgG (F276, Molecular Probes) at a 1100 dilution. Slides were washed three times with 1 ml of 0.5% BSA in 0.05% Tween-20 in PBS in between and after incubations with primary and secondary antibodies. DNA was stained with bisbenzimide, which was included in the secondary antibody solution (3 μg/ml final concentration). Coverslips were mounted on glass slides using Vectashield (Vector), to prevent quenching of fluorescence. Immunofluorescence was detected with a Zeiss epifluorescence microscope, at 40X and 100X, using appropriate filters for detection of rhodamine and bisbenzimide, and via confocal microscopy.

Substantial staining was observed for all three antibodies in the DMSO control, while reduced staining was observed for all three antibodies in cells treated with geldanamycin. For cells treated with GMD-4c, significant reduction in fluorescence levels was only observed for the anti-HER2 antibodies.

We claim:

1. A chemical compound comprising first and second hsp-binding moieties which bind to the pocket of hsp90 with which ansamycin antibiotics bind, said binding moieties being connected to one another by a linker, wherein the first and second hsp-binding moieties are each an ansamycin antibiotic and retain the ability in the chemical compound to bind to the pocket of hsp90.

2. The chemical compound of claim 1 wherein at least one of the hsp-binding moieties is geldanamycin, and the linker is connected to the 17-carbon of the geldanamycin.

3. The chemical compound of claim 2 wherein the linker has a length of 4 to 7 carbon atoms.

4. The chemical compound of claim 1 wherein the first and second hsp-binding moieties are geldanamycin and the linker is connected to the 17-carbons of the geldanamycins.

5. The chemical compound of claim 4 wherein the linker has a length of 4 to 7 carbon atoms.

6. The chemical compound of claim 5 wherein the linker has a length of 4 carbon atoms.

7. A method for destruction of cells expressing a HER-family tyrosine kinase, comprising administering to the cells a chemical compound comprising first and second hsp-binding moieties which bind to the pocket of hsp90 with which ansamycin antibiotics bind, said binding moieties being connected to one another by a linker, wherein the first and second hsp-binding moieties are each an ansamycin antibiotic and retain the ability in the chemical compound to bind to the pocket of hsp90.

8. A method for treating cancer in a patient suffering from cancer, comprising administering to the patient a therapeutic composition comprising a chemical compound comprising first and second hsp-binding moieties which bind to the pocket of hsp90 with which ansamycin antibiotics bind, said binding moieties being connected to one another by a linker, wherein the first and second hsp-binding moieties are each an ansamycin antibiotic and retain the ability in the chemical compound to bind to the pocket of hsp90.

9. The method of claim 8 wherein the cancer is an HER-positive cancer.

10. The method according to claim 8 wherein at least one of the hsp-binding moieties is geldanamycin, and the linker is connected to the 17-carbon of the geldanamycin.

11. The method according to claim 10 wherein the linker has a length of 4 to 7 carbon atoms.

12. The method according to claim 11 wherein the linker has a length of 4 carbon atoms.

13. The method according to claim 8 wherein the first and second binding moieties are geldanamycin, and the linker is connected to the 17-carbons of the geldanamycins.

14. The method according to claim 13 wherein the linker has a length of 4 to 7 carbon atoms.

15. The method according to claim 14 wherein he linker has a length of 4 carbon atoms.

16. The method according to claim 9 wherein at least one of the hsp-binding moieties is geldanamycin, and the linker connected to the 17-carbon of the geldanamycin.

17. The method according to claim 16 wherein the linker has a length of 4 to 7 carbon atoms.

18. The method according to claim 17 wherein the linker has a length of 4 carbon atoms.

19. The method according to claim 7 wherein the first and second binding moieties are geldanamycin, and the linker is connected to the 17-carbons of the geldanamycins.

20. The method according to claim 19 wherein the linker has a length of 4 to 7 carbon atoms.

21. The method according to claim 20 wherein the linker has a length of 4 carbon atoms.

22. The method according to claim 7 wherein at least one of the hsp-binding moieties is geldanamycin, and the linker is connected to the 17-carbon of the geldanamycin.

23. The method according to claim 22 wherein the linker has a length of 4 to 7 carbon atoms.

24. The method according to claim 23 wherein the linker has a length of 4 carbon atoms.

25. The method of claim 8 wherein the cancer is one in which the cancer cells overexpress a HER-family kinase.

26. The method of claim 8 wherein the cancer is breast cancer.

27. The method of claim 8 wherein the cancer is ovarian cancer.

28. The method of claim 8 wherein the cancer is pancreatic cancer.

29. The method of claim 8 wherein the cancer is gastric cancer.

* * * * *

UNITED STATES PATENT AND TRADEMARK OFFICE
CERTIFICATE OF CORRECTION

PATENT NO. : 7,238,682 B1  Page 1 of 1
APPLICATION NO. : 09/937192
DATED : July 3, 2007
INVENTOR(S) : Rosen et al.

It is certified that error appears in the above-identified patent and that said Letters Patent is hereby corrected as shown below:

Column 10, Claim 15, Line 26 should read: --The method according to claim 14 wherein the linker--

Column 10, Claim 16, Line 29 should read: --of the hsp-binding moieties is geldanamycin, and the linker is--

Signed and Sealed this

Fourteenth Day of August, 2007

JON W. DUDAS
*Director of the United States Patent and Trademark Office*

UNITED STATES PATENT AND TRADEMARK OFFICE
CERTIFICATE OF CORRECTION

PATENT NO. : 7,238,682 B1 Page 1 of 1
APPLICATION NO. : 09/937192
DATED : July 3, 2007
INVENTOR(S) : Rosen et al.

It is certified that error appears in the above-identified patent and that said Letters Patent is hereby corrected as shown below:

Column 1, Line 9, insert: This application was supported by NIH ARMY grant numbers CA68425, CA68425-02 and CA28824. The United States government has certain rights in this invention.

Signed and Sealed this

Twenty-second Day of July, 2008

JON W. DUDAS
*Director of the United States Patent and Trademark Office*